United States Patent [19]

Orr

[11] Patent Number: 4,620,866

[45] Date of Patent: Nov. 4, 1986

[54] 2-AZETIDINEACETIC ACID AND CERTAIN OF ITS CONGENERS

[75] Inventor: Alexander F. Orr, Teynham, Nr. Sittingbourne, United Kingdom

[73] Assignee: Shell Oil Company, Houston, Tex.

[21] Appl. No.: 639,986

[22] Filed: Aug. 13, 1984

Related U.S. Application Data

[63] Continuation-in-part of Ser. No. 571,403, Jan. 17, 1984, abandoned.

[30] Foreign Application Priority Data

Jan. 21, 1983 [GB] United Kingdom ............... 8301702

[51] Int. Cl.[4] .................. A01N 43/44; C07D 205/04
[52] U.S. Cl. ......................................... 71/88; 540/200
[58] Field of Search ..................... 260/239 AR; 71/88

[56] References Cited

U.S. PATENT DOCUMENTS 4,047,930 9/1977 Kerr ........................................ 71/95

FOREIGN PATENT DOCUMENTS 29265 5/1981 European Pat. Off. .

OTHER PUBLICATIONS

Britikov, et al., Fisiologia Rasteniya—Plant Physiology, vol. 13, No. 6 (1966) Translation from Russian.

Primary Examiner—Donald G. Daus
Assistant Examiner—William A. Teoli, Jr.

[57] ABSTRACT

2-Azetidinylacetic acid and certain of its congeners and use thereof for sterilizing the male parts of wheat plants.

9 Claims, No Drawings

2-AZETIDINEACETIC ACID AND CERTAIN OF ITS CONGENERS

This application is a continuation-in-part of application Ser. No. 571,403, filed on Jan. 17, 1984 now abandoned.

BACKGROUND OF THE INVENTION

To obtain $F_1$ hybrid seeds, which have advantages over non-hybrid seeds, seed breeders cross-pollinate carefully selected parent plants. Wheat plants have hermaphroditic flowers, and normally self-pollinate. This characteristic can cause a problem in effecting cross-breeding, leading to mixtures of hybrid and non-hybrid seed. The problem has been solved in the past by emasculating (removing the male anthers) each of the flowers of the prospective female parent plant by hand before it is pollinated by pollen from the prospective male parent. Such hand operations are extremely laborious and time-consuming, and require highly-skilled workers. Much research is being carried out with a view to effecting the emasculation by treating the prospective female parent with a chemical, and thus avoiding such hand operations.

DESCRIPTION OF THE INVENTION

It now has been found that 2-azetidineacetic acid and certain of its congeners selectively sterilize the male parts of wheat plants by way of rendering the pollen grains non-functional—i.e., sterile. These azetidine derivatives are described by the formula

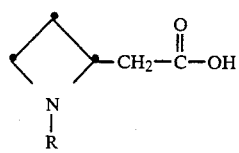

wherein R is hydrogen or acyl —C(O)R$^1$, wherein R$^1$ is hydrogen, straight-chain or branched-chain alkyl of from one to four carbon atoms, phenyl or benzyl.

Because of its effectiveness, the compound wherein R is hydrogen is preferred.

The azetidines of Formula I exist in the form of optical isomers, the carbon atom at the 2-position in the ring being chiral. As is usual in processes involving biological systems, some isomers may be more active in the process of the invention than other isomers. This invention contemplates all of such isomeric forms, as well as mixtures thereof, including those obtained from the method of synthesis employed, and deliberately prepared mixtures.

The present invention comprises these novel compounds a method for sterilizing the male parts of wheat plants, which method comprises applying to a wheat plant, after development of the flowers has begun, but prior to pollen shed, an effective amount of a compound of Formula I, and a method for producing hybrid wheat seed which comprises applying to a candidate female parent wheat plant after development of the flowers has begun, but prior to pollen shed an effective amount of a compound of Formula I, causing the candidate female plant to be pollinated with pollen from a candidate male parent wheat plant, allowing the female parent to mature until the seed is mature, and harvesting the seed. The invention also includes compositions adapted for effecting these methods which comprise an effective amount of a compound of Formula I, an inert carrier and a surface-active agent. The method according to the invention generally produces plants in which male sterility has been induced without an unduly adverse effect upon the female fertility of the plants. The treated plants thus are quite suitable for use in hybrid seed production.

It has been found that compounds of Formula I effect male sterility in wheat plants without unacceptable side-effects, such as phytotoxicity.

It appears that the azetidine has the desired effect when it is applied to the plant at a time during the development of the pollen—i.e., between the time of floral initiation and pollen shed. Preferably, the azetidine is applied somewhat before the pollen is wholly mature, to ensure movement of an effective dosage of the azetidine into the concerned plant tissue, believed to be the pollen grains, in time to effect sterilization of the pollen. In wheat, this "application window" appears to extend from about growth state 32 (second stem node detectable; anthers beginning to differentiate) to about growth stage 49 (awns appearing—i.e., late booting; pollen grains well developed). The definitions and meanings of the numbered growth stages are those set out by D. R. Tottman and R. J. Makepeace, Annals of Applied Biology, 93, 221–234 (1979).

The compound of Formula I is suitably applied a a dosage of from 0.25 to 15 kilograms per hectare, dosages of from 1.0 to 3.0 kilograms per hectare ordinarily sufficing.

The present invention also provides a method for producing $F_1$ hybrid seed which comprises cross-pollinating a wheat plant which has been treated with a compound of Formula I, according to the method of this invention, with pollen from a second untreated wheat plant.

The compound of Formula I will be formulated for use in the method of the invention. The invention, therefore, also provides a pollen-sterilizing composition which comprises the compound of Formula I, together with a suitable carrier and a suitable surface-active agent.

The term "carrier" as used herein means an inert solid or liquid material, which may be inorganic or organic and of synthetic or natural origin, with which the active compound is mixed or formulated to facilitate its application to the plant. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids of aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides. The compositions of the invention may be prepared as wettable powders, dusts, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

In many, if not most, cases, the compound of Formula I is conveniently applied as a water solution containing a small amount of an inert surfactant, a nonionic material being suitable for the purpose. The surfactant of course must be a material that is not toxic to the plant to be treated, at the dosage of the azetidine which is to be used. In such compositions, the concentration of the compound of Formula I suitably is of the order of about 0.01 to about 1 percent by weight of the composition, while the concentration of surfactant is of the order of 0.05 to 2.0 percent (ordinarily about 0.1 to about 1.0 percent), on the same basis.

It is evident from the foregoing that this invention contemplates compositions containing as little as about 0.01% by weight to as much as about 75% by weight of a compound of Formula I as the active ingredient.

Example 1, hereinafter, illustrates a method for preparing 2-azetidineacetic acid (Formula I, R=hydrogen). The N-derivatives of that acid can be prepared by conventional methods, such as treating the acid with the appropriate acid anhydride (such as acetic formic anhydride ($R^1$=hydrogen), acetic anhydride ($R^1$=methyl)), benzoyl chloride ($R^1$=phenyl) or phenylacetic acid chloride ($R^1$=benzyl)).

The following examples illustrate the invention. In each case, the identity of each product ws confined by appropriate chemical and spectral analyses.

EXAMPLE 1

2-Azetidineacetic acid (1)

The methyl ester of DL-(1-benzhydryl-2-azetidine)-carboxylic acid was prepared according to the method of R. M. Rodebaugh and N. H. Cromwell, Journal of Heterocyclic Chemistry, 1969, volume 6, pages 435–437. 9 g of the ester was dissolved in 80 ml of diethyl ether and the solution was added over 20 minutes to a mixture of 2 g of lithium aluminum hydride in 50 ml of diethyl ether. The resulting mixture was stirred at reflux temperature for 2 hours. Then 2 ml of water was added, followed by 2 ml of 15% w/v aqueous sodium hydroxide solution, then 6 ml of water. The resulting mixture was stirred for 1 hour, allowed to stand for 15 hours, and filtered. The solvent was evaporated from the filtrate to give 1-benzyhydryl-2-hydroxymethylazetidine (1A), as an oil.

3.7 g of mesyl chloride was added over 15 minutes to a mixture of the 1A, 3.2 g of triethylamine and 50 ml of toluene, at 0° C. The resulting mixture was stirred for 16 hours at 20° C. and filtered. The solvent was evaporated from the filtrate to give 1-benzyhydryl-2-(mesyloxymethyl)azetidine (1B).

The 1B was dissolved in 120 ml of dimethylformamide and the solution was added over 10 minutes to a saturated solution of sodium cyanide in water (4.7 g NaCN/9 ml $H_2O$) at 65° C. The resulting solution was stirred at 65° C. for 16 hours, then was cooled and poured into water. The mixture was extracted with methylene chloride; the extract was washed with brine, dried and the solvent was evaporated. The residue was chromatographed over silica gel, using a 10% v:v solution of ethyl acetate in light petrol as eluent. The product was recrystallized from methanol to give 1-benzhydryl-2-(cyanomethyl)azetidine (1C), as a crystalline solid, m.p.: 82°–85° C.

A mixture of the 1C, 2.5 g of sodium hydroxide, 36 ml of ethanol and 24 ml of water was refluxed for 6 hours, then left to cool for 16 hours. The mixture then was poured into water, washed with ether and acidified to pH 5. The solvent was evaporated, the residue was taken up in methanol, the solution was filtered and the methanol was evaporated. The residue was dissolved in chloroform; the solution was washed with brine, dried and the solvent was evaporated, to give 1-benzhydryl-2-azetidine carboxylic acid (1D).

5 g of 1D and 0.5 g of a 5% palladium-on-carbon catalyst were shaken in a Parr apparatus at 50° C. and hydrogen pressure of 2.8 atmospheres. The resulting solution was filtered, the solvent was evaporated and the residue was partitioned between water and chloroform. The water phase was separated, washed with chloroform and the water was evaporated. Ethanol was added and evaporated to remove any residual water. The residue was warmed at 1 Torr. pressure to further dry it. The product was recystallized from ethanol to give 1, as a crystalline solid, m.p.: 132°–137° C.

EXAMPLE 2

1-acetyl-2-azetidine acetic acid (2)

2 was prepared as a solid, m.p.: 148°–150° C., by treating 1 with acetic anhydride.

EXAMPLE 3

Demonstration of Pollen-Sterilizing Activity

Spring wheat (*Triticum aestivum*, cv. Sicco) was propagated in a glasshouse or polythene tunnel, in 13 centimeter pots containing a loam-based compost. Supplementary lighting was provided by high-pressure mercury vapor lamps to give a constant day length of 16 hours. The temperature was maintained at approximately 20° C.

The compound to be tested was formulated as an aqueous solution containing 0.4% Triton X 155 (trade mark) as wetting agent and 1% acetone to aid solubility. This formulation was diluted with water and sprayed onto plants to runoff. Treatment rate: 2 kilograms/hectare. The plants were treated at the growth stage when the second node of the plant was just detectable.

At ear emergence but before anthesis, 3 main stem heads from each treated pot were placed in cellophane bags to prevent cross-pollination. At maturity, the bagged ears were harvested, and seed set was recorded and compared with untreated controls. The results are shown in Table I.

TABLE I

| Compound No. | Percent Reduction in Grain Set on Indicated (as compared to Control) at Application Rate 2 kg/ha | |
|---|---|---|
| | Main Stem | Tillers |
| 1 | 85.2 | 74.9 |
| 2 | 13.6 | 7.1 |

It can be seen that both of the test compounds produced a reduction in grain set compared with the untreated controls, clearly illustrating the ability of the compounds to induce male sterility in spring wheat.

EXAMPLE 4

The capability of wheat plants to set seed by cross-pollination, following treatment of the plants with Compound 1, was assessed as follows:

Plants of spring wheat (*Triticum aestivum* cv. Yecora rojo) were grown in pots (four plants per pot) in a greenhouse under controlled conditions for optimum growth. The compound was applied as an aqueous solution containing 0.75% Tween 20 as surfactant, at the rate of 600 liters per hectare. Control plants were sprayed with water containing 0.75% Tween 20. The compound was applied at dosages of 1 and 2 kilograms per hectare, and was applied to the plants during spike development prior to head emergence. The stage of development (length of spike primordia) was determined by measuring the lengths of a random sampling of five spikes. All were in the range of 3.5 to 4.0 centimeters in length (stages 33–43, Zadok's scale).

Following treatment, the plants were placed in a randomized block arrangement, with at least four replicates per treatment and two controls per replicate.

As the spikes emerged, the mainstem of each of the four plants was bagged to prevent cross-pollination. This test determined the overall effect of the test compound upon the flowers of the plants, based upon self-pollination. To determine that the effect was selective, with respect to male parts only, in some cases, half (i.e., two) of the mainstem spikes per pot were hand-crossed with pollen from untreated plants. Control spikes also were handcrossed.

When the developing seeds reached the soft dough stage, water was withheld, to dry the seeds for harvest, and the number of seeds that had been set were counted. The following results were obtained.

TABLE II

| Rate (kg/ha) | Head Description | Seed Set (Percent Compared to the Control) |
|---|---|---|
| 1 | Main Stem | 34 |
| | Cross-pollinated | 86 |
| 2 | Main Stem | 10 |
| | Cross-pollinated | 70 |

The compounds of Formula I have been found to be nonphytotoxic to wheat plants at the dosages required to effect sterilization of the male parts of the plants.

I claim:

1. A compound of the formula:

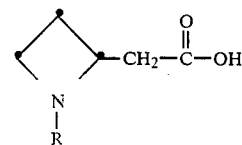

wherein R is hydrogen, acyl —C(O)R$^1$, wherein R$^1$ is hydrogen, straight-chain or branched-chain alkyl of from one to four carbon atoms, phenyl or benzyl.

2. A compound according to claim 1 wherein R is hydrogen.

3. A method for sterilizing the male parts of a wheat plant, which comprises applying to the plant prior to pollen shed an effective dosage of a compound of claim 1.

4. A method according to claim 3 wherein the compound of claim 1 is that wherein R is hydrogen.

5. A composition of matter adapted for effecting the method of claim 3 comprising an effective amount of a compound of claim 1 together with an inert carrier and a surface-active agent.

6. A composition of matter according to claim 5 wherein the carrier is water and the surface-active agent is a nonionic material.

7. A composition of matter according to claim 6 wherein the compound of claim 1 is that wherein R is hydrogen.

8. A method for producing a hybrid wheat seed which comprises applying to a candidate female parent wheat plant prior to pollen shed an effective dosage of a compound of claim 1, causing the candidate female plant to be pollinated with pollen from a candidate male parent plant, allowing the female parent to mature until the seed is mature, and harvesting the seed.

9. A method according to claim 8 wherein the compound of claim 1 is that wherein R is hydrogen.

* * * * *